United States Patent [19]

Katz

[11] 4,044,055

[45] Aug. 23, 1977

[54] PROCESS FOR MANUFACTURE OF TETRAKIS-(HYDROXYMETHYL)-PHOSPHONIUM SALTS

[75] Inventor: Daniel Stanley Katz, Norwalk, Conn.

[73] Assignee: American Cyanamid Company, Stamford, Conn.

[21] Appl. No.: 635,521

[22] Filed: Nov. 26, 1975

[51] Int. Cl.$^2$ .............................................. C07F 9/54
[52] U.S. Cl. .............................. 260/606.5 F; 260/541; 260/606.5 P
[58] Field of Search .................. 260/606.5 F, 606.5 P, 260/541

[56] References Cited

U.S. PATENT DOCUMENTS

| | | | |
|---|---|---|---|
| 2,743,299 | 4/1956 | Flynn et al. | 260/606.5 F |
| 3,013,085 | 12/1961 | Buckler | 260/606.5 F |
| 3,243,450 | 3/1966 | Grayson | 260/606.5 F X |
| 3,666,817 | 5/1972 | Carlson | 260/606.5 F |
| 3,835,194 | 9/1974 | Leavitt | 260/606.5 F |

*Primary Examiner*—Helen M. S. Sneed
*Attorney, Agent, or Firm*—Gordon L. Hart

[57] ABSTRACT

Tetrakis-(hydroxymethyl)-phosphonium salts (TKX salts) are produced by countercurrent contacting of phosphine gas with aqueous solution of formaldehyde and a selected acid in a multistage reactor. In the countercurrent contacting reactor, phosphine is practically exhausted at the liquid feed end while at the other end the formaldehyde is exhausted. When the formaldehyde end point is exceeded in the reactor, phosphine reacts with product TKX salt to produce trihydroxymethylphosphine (THP). Product taken from the reactor is adjusted to end point by addition of formaldehyde as needed to convert THP to TKX.

6 Claims, 1 Drawing Figure

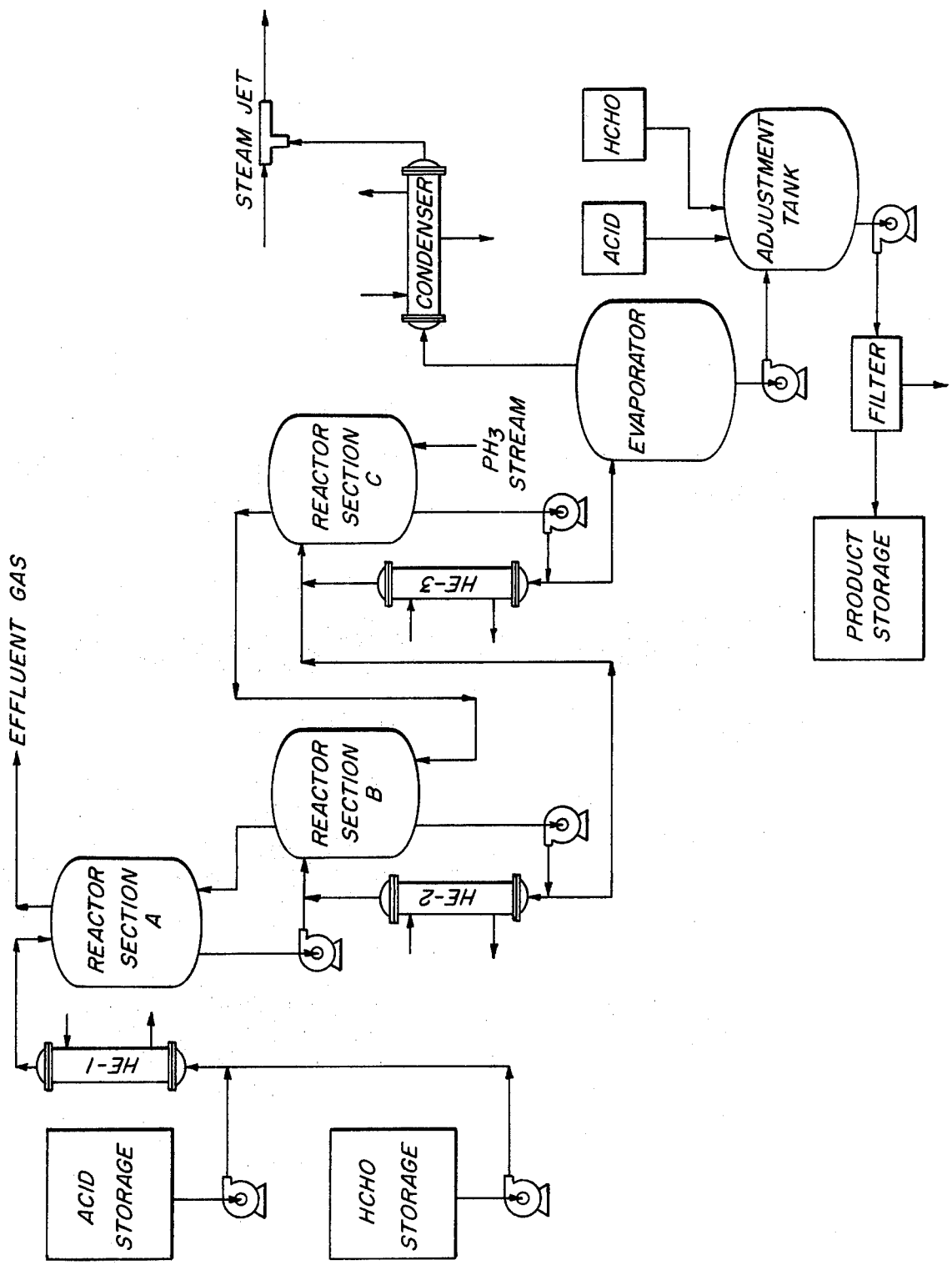

PROCESS FOR MANUFACTURE OF TETRAKIS-(HYDROXYMETHYL)-PHOSPHONIUM SALTS

The invention relates to chemical synthesis of tetrakis-(hydroxymethyl)-phosphonium salts by the reaction of phosphine with formaldehyde and a selected acid.

It is known to prepare tetrakis-(hydroxymethyl)-phosphonium salts (TKX salts) by reaction of phosphine, formaldehyde and a selected acid such as hydrochloric acid, sulfuric acid, phosphoric acid, oxalic acid, acetic acid and the like. Selection of the acid reactant will determine the particular anion of the salt product. U.S. Pat. No. 2,743,299, patented Apr. 24, 1956 described the production of tetrakis-(hydroxymethyl)-phosphonium chloride by contacting aqueous liquid solution of formaldehyde and hydrochloric acid with a gas stream of phosphine in a reactor designed for gas-liquid contacting. U.S. Pat. No. 3,835,194 described a similar process using higher reaction temperature for the synthesis of tetrakis-(hydroxymethyl)-phosphonium oxalate by contacting gaseous phosphine with a liquid aqueous solution of oxalic acid and formaldehyde in a packed column reactor which provided gas-liquid contact of the reactants by countercurrent flow of the gas and liquid streams.

The process of the invention employs a counter-current gas-liquid contacting reactor having at least three separate contacting stages in separate reactor sections arranged for continuous reaction with countercurrent contacting of the gas and liquid reactant streams. In the first contacting stage, a fresh liquid feed of aqueous formaldehyde and acid is contacted with the relatively small amount of unreacted phosphine which remains in the countercurrent gas stream after it has traversed the other stages in the reactor. In the last contacting stage the fresh, full phosphine gas feed stream is contacted with the countercurrent liquid stream which has traversed the other stages in the reactor. In this last stage, the liquid feed stream contains TKX product with the reduced concentrations of unreacted formaldehyde and acid which remain in the solution from the previous contacting stages. The use of a multiple stage reactor permits easier process control and reduces the contacting capacity needed to assure that the phosphine feed is continuously consumed and that the reaction is continuously carried to at least the formaldehyde end-point or just slightly beyond, all within the reactor. The intermediate contacting stage or stages within the reactor are used to carry out the bulk of the reaction while the first and last stages are used for the final consumption of the respective reactants. In the preferred embodiment, a single intermediate stage is all that is needed.

It is advantageous to completely react all of the phosphine within the reactor, thereby avoiding the problem of disposing of off-gas that would contain phosphine. In any case, residual phosphine should not exceed 3 percent of the total phosphine fed to the reactor. In a typical operation of the process of this invention, the phosphine consumed within the reactor is practically complete, better than 99.5 percent of the total phosphine feed in most instances.

The rate of reaction will be accelerated by increase in temperature and also by increase in pressure. The reactor can be safely operated at temperatures up to about 75° C. in most instances and we find that the process can be operated economically at reaction temperatures in the range from about 40° C. up to about 75° C. For most of the reactions the most preferred reaction temperature is about 60°–65° C. The reaction can be carried out at pressures up to about 100 psia when equipment is available for operation at that pressure. A more convenient range of pressures for operation of the reactor is in the range from about 35 to about 50 psia.

Product TKX salt is taken from the reactor continuously as an aqueous solution of the product from the last contacting stage. To simplify the finishing of this product solution to meet commercial specification, it is preferred to completely consume all or as much as possible of the formaldehyde and acid reactants in the product solution before it leaves the reactor. This eliminates the need to remove residues of those reactants after the product solution leaves the reactor. For this purpose, the formaldehyde and acid reactants are added to the liquid feed solution in amounts as close as practicable to the stoichiometric ratio for this reaction, i.e. four molar parts aldehyde to one equivalent part of the acid. We prefer to mix to always achieve the full stoichiometric equivalent or slight excess of formaldehyde (4.0 to 4.1 moles) with respect to the acid in this feed solution. To allow for errors we measure 4.05 moles formaldehyde per equivalent weight of acid. To the same end, the reaction is operated in the last contacting stage to always reach or slightly exceed an end-point at which the last of the formaldehyde reactant has been consumed from the solution by reaction. After that end-point has been reached in the reactor, further contacting of the product solution with phosphine will cause the TKX salt to react with additional phosphine to produce tris-hydroxymethyl-phosphine (THP). This latter reaction is expressed by the equation:

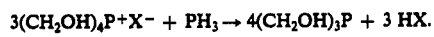

$$3(CH_2OH)_4P^+X^- + PH_3 \rightarrow 4(CH_2OH)_3P + 3 HX.$$

To a solution containing small amounts of THP may be added formaldehyde, with acid when needed, which will cause conversion of THP back to the TKX salt by the reaction expressed by the equation:

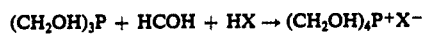

$$(CH_2OH)_3P + HCOH + HX \rightarrow (CH_2OH)_4P^+X^-$$

The invention takes advantage of both of these reactions to achieve the exact end-point. When operating the reactor continuously, it is practically impossible to continuously maintain the composition of the product stream at the exact end-point. However, the product solution is easily adjusted to the end-point in batch operations after the product solution has been taken from the reactor. This can be accomplished by analysis of a sample taken from a batch of the product solution and addition to the product solution of small amounts of either phosphine or the aldehyde and acid reactants in the amounts needed to reach the end-point. In the process of the invention the reactor is operated continuously with regulation so that the reaction with phosphine in the last stage always runs at least to or beyond the end-point. In this mode of operation, the reactor produces a product solution that will contain a small amount of THP and no formaldehyde. This eliminates the need for ever having to use phosphine gas for the end-point adjustment outside the reactor. It is then a relatively simple matter to analyze the product solution in batches for THP and acid and then adjust to the end-point for each batch by the addition of the calculated amounts of formaldehyde and acid that are needed to convert the THP in solution to TKX salt.

Removal of water from the product solution as may be needed to concentrate the product solution to specification, is carried out by evaporation preferably in an evaporator with pressure reduced. The evaporation may be carried out either before or after the final end-point adjustment. Filtration of the product solution prior to storage is also preferred for improvement of product quality.

The invention will be further explained with reference to detailed description of a specific example embodying the invention. The invention may be carried out with some variations from the strict detail of this example, and mention will be made of some particular variations that might be made within the broader scope of the invention.

A schematic flow diagram of a preferred process embodying the invention is shown in the drawing.

Referring to the drawing, the reactor is shown consisting of three sections, A, B and C. Reactor Section A is the fresh liquid feed section in which the first contacting stage is carried out. Formaldehyde aqueous solution taken from HCHO Storage and acid aqueous solution taken from Acid Storage are mixed in stoichiometric amounts and heated to a temperature below the design reaction temperature in a heat exchanger HE-1 and the mixture is fed continuously to Reactor Section A. The residue phosphine gas stream that is taken from Reactor Section B is fed continuously as the gas feed stream into Reactor Section A where the phosphine is contacted with the agitated liquid in Reactor Section A for reaction of the phosphine with formaldehyde and acid reactants which are in the fresh liquid feed solution. Section A could be the uppermost section of a multistage countercurrent gas-liquid contacting column, located above Section B in the same column, but we prefer to use for Section A a separate pressure kettle reactor equipped with an agitator and a gas sparge. Similarly, Reactors B and C might be intermediate and lower sections respectively in a multistage countercurrent gas-liquid contacting column. In such a reactor column each section would have to be equipped with means for either internal or external control of liquid temperature within each section and with means for recirculation of the liquid phase in each section. As with Section A, we again prefer to use separate pressure kettles equipped with agitators and gas sparges for each of the Reactor Sections B and C. These two kettles are further equipped with separate liquid temperature control means for each section. Liquid taken from Reactor Section A is continuously fed to the liquid agitation chamber in Reactor Section B while gas taken from Reactor Section C is continuously fed to the gas sparge in Reactor Section B. In each stage the gas is fed through a gas sparge below the liquid level while the liquid is continuously agitated in each kettle. The reaction is exothermic and the temperature in the Reactor Section B is controlled by continuously circulating liquid from Section B through the heat exchanger HE-2 for heat removal. Internal coolers installed inside the reactor could be used instead. Liquid taken continuously from Section B is continuously fed to Reactor Section C where the liquid is contacted with fresh phosphine gas which is fed continuously into the agitated liquid by means of a gas sparge. Temperature is controlled in Section C by continuous liquid circulation through a heat exchanger, HE-3. Internal coolers inside the reactor could be used instead. Means for maintaining pressure in the reactor are not shown in the drawings but this is done by conventional apparatus and means for maintaining fluid pressure up to about 50 to 100 psia in all of the reactor sections. The liquid product solution taken continuously from Reactor Section C is led to a vacuum evaporator where water is removed at evaporation temperature below 75° C. to make 80 percent TKX salt aqueous solution, or to make a more or less concentrated product solution of whatever composition is desired. Before or after the evaporator, the product solution is led to an adjustment tank for batch adjustment of the final product composition to end-point, as described above.

While the reactor is operated continuously, the evaporator may be operated either continuously or in batch modes. In either case one may provide means for liquid hold-up before or after the evaporator, or both, and the liquid hold-up may be used as a batch adjustment tank. One may provide two batch evaporators which are operated alternately, one filling as the other is operated to evaporate. We prefer another mode of operation using a single continuous evaporator while providing two batch hold-up tanks for alternate filling before the evaporator and two more after the evaporator. Any of these hold-up tanks may be used as the batch adjustment tank. The product, after evaporation, adjustment and filtering can meet product specification for most commercial uses without further processing.

The process of the invention can be used for making a variety of salts such as tetrakis-(hydroxymethyl)-phosphonium sulfate using sulfuric acid in the product feed or tetrakis-(hydroxymethyl)-phosphonium chloride using hydrochloric acid or tetrakis-(hydroxymethyl)-phosphonium acetate using acetic acid or tetrakis-(hydroxymethyl)-phosphonium phosphate using phosphoric acid or tetrakis-(hydroxymethyl)-phosphonium oxalate using oxalic acid, or it can be used for making TKX mixed salts by using a mixture of two or more of such acids in the liquid feed mixture. One such mixed salt is a phosphate acetate mixed salt made with equivalent weights of each of phosphoric and acetic acid in the feed mixture.

In variations of the invention, the Reactor Section B might be constituted as several actual separate contacting stages in which the greater proportion of the reaction is carried out. For each of the first and last contacting stages it is required to provide contacting capacity sufficient to exhaustphosphine and formaldehyde, respectively, from the gas and liquid streams in these stages. Accordingly, it is preferred that most of the two reactants that have to be exhausted in the first and last stages, be removed from the respective streams by reaction in one or several intermediate reactor stages, to avoid an excessive requirement for contacting capacity in either of those first and last stages.

The amount of water to be used in the process is determined by the amount needed to keep the formaldehyde in solution throughout the process. For the formaldehyde supply we prefer to use a commercially available solution of either 37 percent or 44 percent formaldehyde aqueous solution, which also contains about 1 percent methanol. The acid is dissolved into this solution to make the fresh liquid feed. When more concentrated solutions of formaldehyde are used, the addition of acid may cause precipitation which is undesirable in the liquid feed solution. The methanol is not reactive in the process and is removed in the evaporation step when the product solution is concentrated.

In a typical reactor design according to the schematic flow diagram shown in the drawing, the following approximate flow rates are used, expressed in units of wt. per unit of time. The fresh phosphine feed in the gas stream to the reactor is 16 units. This stream is fed to the gas sparge in Reactor Section C. The fresh liquid feed to Reactor Section A contains 57 units formaldehyde, 17.2 units HCl, 126 units H$_2$O and 1.4 units methanol. Temperature of the gas feed is 40° C. The fresh gas stream contains about 2 percent by wt. of mixed water vapor, hydrogen and nitrogen. Temperature of the fresh liquid feed is 55° C. The gas stream from Reactor Section C is fed directly to the gas sparge in Reactor Section B. It contains 11 units phosphine with small amounts of water, hydrogen and nitrogen. The temperature of that stream is 65° C. The liquid feed to Reactor Section B is the liquid taken from Reactor Section A. It contains 55 units formaldehyde, 17 units HCl, 125 units water and 2.8 units of the product tetrakis-(hydroxymethyl)-phosphonium chloride. The gas stream taken from Reactor Section B and fed to Reactor Section A contains 0.5 units phosphine and about 0.3 units of other gases. The gas stream taken from Reactor Section A is about 0.17 units with less than 0.1 units of phosphine. This waste stream is disposed of by suitable means such as combustion in an incinerator followed by an aqueous scrubber. The liquid stream taken from Reactor Section B and fed to Reactor Section C contains 18 units formaldehyde, 5.4 units HCl, 125 units water, 1.4 units methanol and 62 units tetrakis-(hydroxymethyl)-phosphonium chloride. The product liquid stream from Reactor Section C contains no formaldehyde and no HCl. It contains 90 units tetrakis-(hydroxymethyl)-phosphonium chloride and 125 units water with 1.4 units methanol.

For cooling the liquid in Reactor Section B, liquid from the same reactor section is constantly circulated through a heat exchanger at a rate of about 4400 units, cooling the liquid to about 55° C. for return to Reactor Section B. For cooling the liquid in Reactor Section C, liquid from the same reactor section is constantly circulated through a heat exchanger at a rate of 2100 units, cooling the liquid to about 55° C. for return to same reactor section. Cooling in Reactor Section A can usually be provided adequately without recirculation merely by reducing the feed liquid temperature as needed to maintain the desired reaction temperature in this stage.

The foregoing material balance assumes that the end-point is attained exactly in Reactor Section C. In actual practice the feed amounts are not so exactly controlled and the reactor is operated so that the end-point is usually exceeded. Consequently, a small part of the TKX in the liquid is converted by contact with phosphine in Reactor Section C to make a small amount of tris-(hydroxmethyl)-phosphine in the product liquid stream. The pressure in the Reactor Sections is maintained at about 40 psia by suitable pressure means. The residence time of the liquid stream in a reactor of the above design is about 90 minutes.

From the foregoing material balance it will be seen that the Reactor Section A produces only about 3 percent of the product but it practically exhausts the phosphine gas reactant. Section C produces about one third of the product and exhausts all of the liquid reactants from the liquid stream. The essential function of each of these two end stages is to provide the contacting capacity needed to exhaust the reactants from the gas and liquid streams, respectively, after they are taken from the intermediate stage in which most of the reaction product is made.

The 42 percent product solution taken from Reactor Section C is led to two batch hold-up tanks where it is held for feed to a continuous vacuum evaporator which is operated at about 2 psia pressure and about 75° C. In the evaporator the concentration is increased to about 80 percent TKC by evaporation of water and methanol from the solution. This concentrate is taken from the evaporator to two other hold-up tanks where it is held for feed to filters. The hold-up tanks both before and after the evaporator are equipped with means for metering formaldehyde and acid into the tanks so that any of the hold-up tanks may be used for the batch adjustment to end-point as described above. From the filters, the product is taken to storage. Other TKX salt solutions are prepared by the same process using other acids in equivalent amounts instead of the hydrochloric acid used in the foregoing specific examples.

I claim:

1. A process for synthesis of tetrakis-(hydroxymethyl)-phosphonium salt by reaction of phosphine reactant in a continuously flowing gas stream with a mixture of formaldehyde reactant and acid reactant in a continuously flowing liquid stream by continuously contacting said gas and liquid streams countercurrently in a multiple-stage series of at least three separate gas-liquid contacting reactor stages, each of said separate reactor stages comprising a pressure kettle having sparging means by which the part of the gas stream in said kettle is sparged through the part of the agitated liquid stream in said kettle as said respective streams are fed continuously through said series of separate stages.

2. A process defined by claim 1 comprising a first reactor stage in which residual phosphine in the gas stream entering the first stage is reduced to less than three percent of the total phosphine feed by reaction in said first stage of phosphine with the fresh liquid feed stream entering said first stage and a last reactor stage in which residual formaldehyde in the liquid stream entering said last stage is completely consumed by reaction of the formaldehyde and acid reactants in said liquid stream with phosphine in the fresh phosphine gas stream entering said last stage.

3. A process defined by claim 2 wherein phosphine is further reacted in said last reactor stage with a small proportion of the tetrakis-(hydroxymethyl)-phosphonium salt product in the liquid stream to produce a small amount of tris-(hydroxymethyl)-phosphine in the liquid stream leaving said last stage.

4. A process defined by claim 3 further comprising a step of adjusting the composition of the liquid product solution after it has been taken from the defined last stage by adding formaldehyde and acid in calculated amounts that will just convert the small amount of tris-(hydroxymethyl)-phosphone in said solution to the tetrakis-(hydroxymethyl)-phosphonium salt.

5. A process defined by claim 1 wherein the defined reaction is carried out at reaction temperature in the range from about 40° C. to about 75° C. and at pressure from about 35 psia to about 100 psia.

6. A process defined by claim 2 wherein the major part of the reactants in both the gas and liquid countercurrent streams are consumed by reaction in at least one separate intermediate contacting stage between the defined first and last contacting stages.

* * * * *